United States Patent
Zeijlemaker et al.

(10) Patent No.: US 7,660,620 B2
(45) Date of Patent: Feb. 9, 2010

(54) TIMING TECHNIQUES FOR MAGNETIC RESONANCE IMAGING

(75) Inventors: Volkert A. Zeijlemaker, Landgraaf (NL); Steven D. Goedeke, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 349 days.

(21) Appl. No.: 10/673,777

(22) Filed: Sep. 29, 2003

(65) Prior Publication Data

US 2005/0070786 A1 Mar. 31, 2005

(51) Int. Cl.
A61B 5/05 (2006.01)
(52) U.S. Cl. .................. 600/411; 600/407; 600/423; 607/2; 607/60; 607/33; 607/52
(58) Field of Classification Search ......... 600/407–423; 607/2–9, 60, 33, 52
See application file for complete search history.

(56) References Cited

U.S. PATENT DOCUMENTS

| 5,217,010 A | 6/1993 | Tsitlik et al. |
| 5,629,622 A | 5/1997 | Scampini |
| 5,697,958 A * | 12/1997 | Paul et al. ............... 607/31 |
| 6,304,777 B1 | 10/2001 | Ben-Haim et al. |
| 6,442,424 B1 | 8/2002 | Ben-Haim et al. |
| 6,711,436 B1 | 3/2004 | Duhaylongsod |
| 6,925,328 B2 * | 8/2005 | Foster et al. ............... 607/9 |
| 6,937,906 B2 * | 8/2005 | Terry et al. ............... 607/63 |
| 2002/0032468 A1 | 3/2002 | Hill et al. |
| 2002/0133199 A1 | 9/2002 | MacDonald et al. |
| 2003/0109901 A1 * | 6/2003 | Greatbatch ............... 607/9 |

OTHER PUBLICATIONS

Nahrendorf et al., "Pacing in High Field Cardiac Magnetic Resonance Imaging: Implantation of a Permanent Pacemaker into a Rat", *Pace*, vol. 27, 671-674, May 2004.
Ennis et al., "Respiratory and Cardiac Grated 3D Imaging for Improved Spatial and Temporal Resolution", *Prac. Intl. Soc. Mag. Reson. Med* 10 (2002).
Prinzen et al., "Mapping of Regional Myocardial Strain and Work During Ventricular Pacing: Experimental Study Using Magnetic Resonance Imaging", *Journal of the American College of Cardiology*, vol. 33, No. 6, 1735-1742, 1999.
Domoulin et al., "Real-Time Position Monitoring of Invasive Devices Using Magnetic Resonance", *Magnetic Resonance in Medicine*, No. 3, 411-415; Mar. 29, 1993; Duluth, Minnesota.
Tanaka et al., "A Gating $^{31}$P NMR Method Triggered by Pulses for Cardiac Pacing", *NMR In Biomedicine*, vol. 5, 329-334, 1992.

* cited by examiner

*Primary Examiner*—Brian Casler
*Assistant Examiner*—John F Ramirez
(74) *Attorney, Agent, or Firm*—Michael J. Ostrom; Reed A. Duthler; Stephen W. Bauer

(57) ABSTRACT

The invention is directed to techniques in which magnetic resonance imaging (MRI) is coordinated with the operation of an implantable medical device (IMD). By using an IMD to sense conditions, MRI can be improved because the sensed conditions can accurately define timing for application of electromagnetic radiation bursts. Moreover, by applying stimulation pulses specifically to coordinate the electromagnetic radiation bursts, the MRI may also be improved.

14 Claims, 5 Drawing Sheets

TIMING TECHNIQUES FOR MAGNETIC RESONANCE IMAGING

FIELD OF THE INVENTION

The invention relates to magnetic resonance imaging (MRI) techniques.

BACKGROUND OF THE INVENTION

Magnetic resonance imaging (MRI) techniques make use of electromagnetic fields to create images of a patient. MRI techniques permit the generation of high-quality two- or three-dimensional images of a patient's body, which can then be examined by a physician for diagnosis purposes. In particular, MRI techniques permit the generation of internal images of a patient's flesh, blood, bones, cartilage, blood vessels, organs, and the like. The generated images can then be examined by physicians in order to diagnose disease, disorders or injuries, and facilitate patient care.

MRI devices typically subject a patient to a very strong static magnetic field and a pulsed gradient magnetic field, and then apply pulses or bursts of electromagnetic radiation (typically radio frequency (RF) radiation bursts) to an area of the patient to be imaged. The strong magnetic field generally orients the protons of the patient's tissue in particular directions. However, the RF radiation bursts cause some of the patient's protons to resonate, or spin, at a particular frequency depending on the local magnetic field during application of the radiation burst. The resonance frequency in MRI is referred to as the Larmour frequency which has a relationship with the local magnetic field. When the RF radiation burst is terminated, the resonating protons reorient themselves in accordance with the strong magnetic field of the MRI device, giving off energy in the process. The MRI device can detect the energy given off by the reorienting protons in order to create a high quality image of the patient's tissue.

In some cases, application of the RF radiation bursts must be timed specifically with a patient's physical body rhythm. For example, when using MRI to image a patient's heart, each burst should be timed for application at a common point of the sinus rhythm. In other words, each of a series of MRI electromagnetic radiation bursts and gradient fields may need to be applied when the heart is in a similar state, i.e., in the same stage of the cardiac cycle. In order to monitor or measure the condition of the heart to facilitate timing of the electromagnetic radiation bursts, MRI techniques typically make use of surface electrocardiograms (ECGs). The ECGs provide measurements of the sinus rhythm and thereby facilitate the coordination of electromagnetic radiation bursts at common times during the cardiac cycle. Surface ECGs, however, can sometimes provide inaccurate cardiac measurements. Moreover, the electromagnetic radiation bursts used for MRI may significantly affect ECG readings such that accuracy of the measurements are undermined during the MRI.

BRIEF SUMMARY OF THE INVENTION

In general, the invention is directed to techniques in which an implantable medical device (IMD) is used to sense or simulate a patient in order to coordinate magnetic resonance imaging (MRI). The conditions sensed by an IMD may be much more accurate than surface electrocardiograms (ECGs) conventionally used to coordinate MRI. Thus, by using an IMD to sense conditions in place of or in addition to surface ECGs, MRI can be improved.

In some cases, IMD stimulation pulses may be applied specifically to coordinate the MRI. In other words, stimulation pulses may be applied in coordination with the application of MRI electromagnetic radiation bursts and gradient fields. The stimulation pulses may help place the patient into the proper contraction phase in order to ensure that the electromagnetic radiation bursts and gradient fields are applied at common times in the rhythm. For example, in the case of a pacemaker, pacing pulses may be applied in coordination with the application of MRI electromagnetic radiation bursts to help ensure that the heart is in a common contraction phase during each burst. In some cases, the IMD may communicate sensing or stimulation information to the MRI device, and in other cases, the MRI device (or a programmer) may instruct the IMD to deliver particular stimulation pulses. In either case, IMD operation can be used to coordinate the application of MRI electromagnetic radiation bursts and gradient fields at proper times for effective imaging.

Conventionally, patients that use IMDs are generally discouraged or prohibited from being subjected to MRI. In particular, the strong magnetic fields associated with MRI techniques may interact with the components of the IMD, possibly causing movement of the IMD within the patient because of magnetic attraction or repulsion. The interaction of the strong magnetic field to the IMD may cause trauma to the patient. However, reductions in the mass of IMDs, as well as use of non-magnetic material or other selected material in IMD construction may reduce or eliminate the interaction of such magnetic fields with the IMD. Accordingly, use of the monitoring and/or stimulating functions of an IMD can provide benefits in MRI applications.

In one embodiment, the invention provides a method of performing MRI comprising receiving information from an IMD, and performing the MRI based on the information.

In another embodiment, the invention provides a method of performing MRI comprising stimulating a patient with an IMD, communicating information indicative of a timing of the stimulation, and performing the MRI based on the information.

In another embodiment, the invention provides a method of performing MRI comprising sending information to an IMD to define operation of the IMD during MRI, and performing the MRI in coordination with operation of the IMD.

In another embodiment, the invention provides an MRI device comprising a magnet to generate a magnetic field, an electromagnetic radiation source to apply electromagnetic radiation bursts, an imaging unit to generate images of patient following application of radiation bursts, a telemetry unit to receive information from an IMD, and a control unit to coordinate application of the electromagnetic radiation bursts based on the information.

In another embodiment, the invention provides a medical device comprising a control unit to coordinate application of MRI electromagnetic radiation bursts with operation of an IMD, and a transmitter to transmit information to the IMD to cause the IMD to operate in coordination with an MRI device.

In another embodiment, the invention provides a system comprising an MRI device to image a patient using electromagnetic radiation bursts, and an IMD, wherein application of the electromagnetic radiation bursts by the MRI device is coordinated with operation of the IMD.

In another embodiment, the invention provides an apparatus comprising means for receiving information from an IMD, and means for performing MRI based on the information.

The different embodiments may be capable of providing a number of advantages. For example, the conditions sensed by an IMD may be more accurate than surface ECGs conventionally used to coordinate MRI. Thus, by using an IMD to sense conditions in place of, or in addition to surface ECGs, MRI can be improved. Moreover, by actively stimulating a patient in coordination with MRI electromagnetic radiation bursts, MRI can be improved.

In some cases, the stimulation may be used to invoke a normal sinus rhythm in coordination with application of MRI electromagnetic radiation bursts. The stimulation may also terminate or induce an arrhythmia in coordination with application of the MRI electromagnetic radiation bursts in order to allow diagnosis of the arrhythmia. In other cases, the stimulation may define fast, slow, or even irregular rhythms in the patient, specifically to enable certain types of MRI imaging. These or other types of triggered stimulation could be very useful for MRI applications.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

The invention is directed to techniques for coordinating the operation of an implantable medical device (IMD) with magnetic resonance imaging (MRI) techniques. Such coordination may improve use of MRI techniques on patients that have an IMD. In particular, techniques are described in which an IMD is used to sense or stimulate a patient in order to coordinate the MRI. The conditions sensed by an IMD may be more accurate than surface electrocardiograms (ECGs) conventionally used to coordinate MRI. Thus, by using an IMD to sense conditions in place of or in addition to surface ECGs, MRI can be improved.

Also, IMD stimulation pulses may be specifically applied to coordinate the MRI. The stimulation pulses can help place the patient into the proper rhythm to ensure that the electromagnetic radiation bursts and gradient fields are applied at common times in the rhythm. For example, in the case of a pacemaker, pacing pulses may be applied in coordination with the application of MRI electromagnetic radiation bursts and gradient fields in order to ensure that the heart is in the proper interval of the cardiac cycle when the bursts and gradient fields are applied, e.g., to ensure that imagining of the heart occurs when the heart is in a particular state. The IMD may communicate sensing or stimulation information to the MRI device, or the MRI device (or a programmer) may instruct the IMD to deliver particular stimulations consistent with MRI techniques to be applied. In either case, IMD operation can be used to coordinate the application of MRI electromagnetic radiation bursts and gradient fields at proper times for effective imaging.

Figure 1:
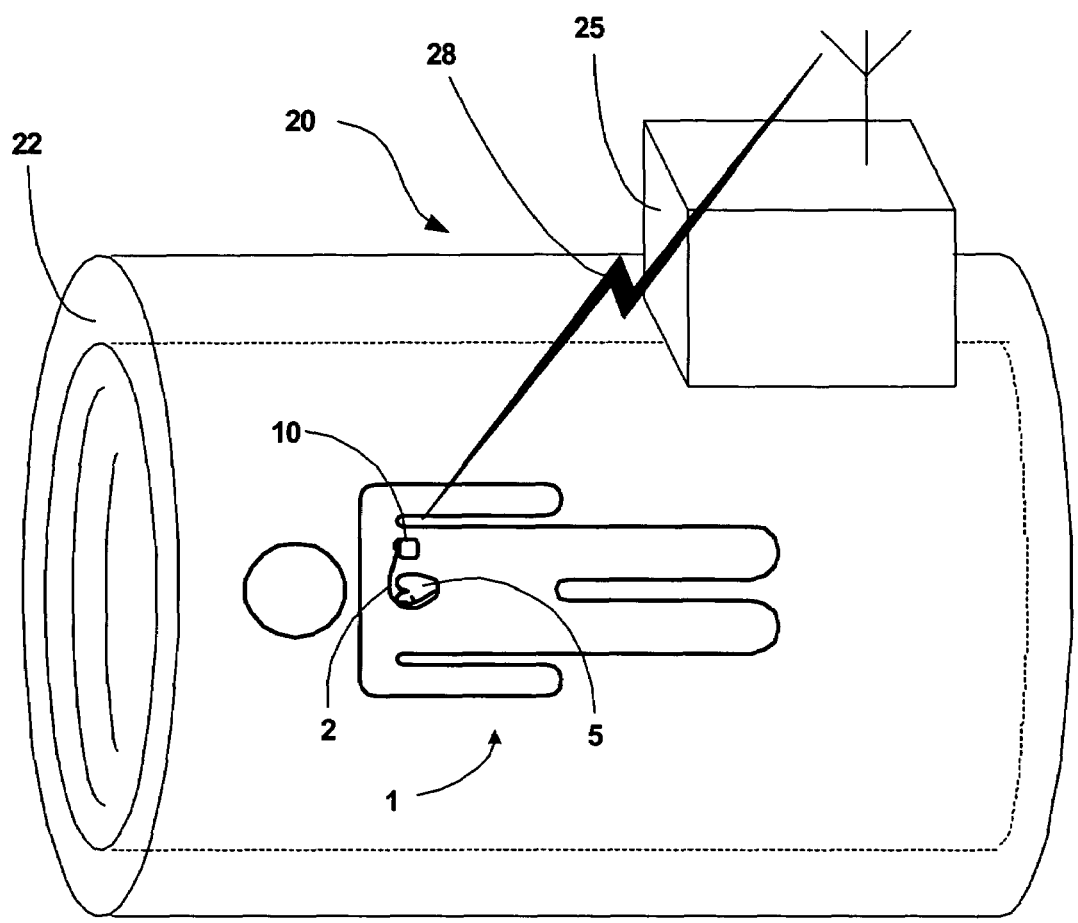
FIG. 1 is a conceptual diagram illustrating a magnetic resonance imaging (MRI) device communicating with an implantable medical device (IMD).

FIG. 1 is a conceptual diagram of a patient 1 inside an MRI device 20. Patient 1 has an IMD. By way of example, the IMD is illustrated as a cardiac pacemaker 10 that provides therapeutic stimulation to heart 5. However, in accordance with the invention, an IMD may generally comprise any of a wide variety of medical devices that can be implanted in the body of a human or other life form. For example, an IMD may alternatively take the form of an implantable cardioverter, an implantable defibrillator, or an implantable cardiac pacemaker-cardioverter-defibrillator.

In alternative applications, one or more of the techniques described herein may be useful to coordinate MRI techniques with other IMDs, such as patient monitoring devices, or devices that integrate monitoring and stimulation features. Also, the invention may find use with a neurological device such as a deep-brain stimulation device or a spinal cord stimulation device. In other applications, the invention described herein may be used with devices that provide muscular stimulation therapy, gastric system stimulation, nerve stimulation, lower colon stimulation, drug or beneficial agent dispensing, recording or monitoring, gene therapy, or the like. In short, the techniques described herein for coordinating MRI techniques with IMD operation may find useful applications in any of a wide variety IMDs.

In the exemplary embodiment illustrated in FIG. 1, pacemaker 10 may deliver pacing pulses to a patient via electrodes disposed on distal ends of one or more leads 2. In other words, one or more leads 2 may position one or more electrodes with respect to various cardiac locations so that pacemaker 10 can deliver pulses to the appropriate locations. The electrodes may also sense electrical events in the heart, which can be monitored or recorded by pacemaker 10.

MRI device 20 may assume a wide variety of shapes, sizes or configurations. In the illustrated example, MRI device 20 defines a relatively large tubular cavity 22 into which patient 1 can be placed during performance of the MRI techniques. In other cases, however, MRI device 20 may define a much smaller cavity, e.g., for insertion of a patients arm, leg, head, or the like. MRI device 20 may assume a wide variety of shapes and sizes and may allow access to a patient during the scan. In any case, MRI device 20 includes a set of MRI components inside housing 25, such as circuitry, magnets, and the like, that support operation of MRI device 20.

MRI device 20 makes use of electromagnetic fields to create images of patient 1. For example, MRI device 20 may subject a patient to very strong static magnetic fields and gradient fields via one or more permanent magnets or electromagnets located about cavity 22 or within housing 25. MRI device 20 then applies radiation bursts, e.g., pulses of electromagnetic radiation (typically radio frequency (RF) radiation) to an area of the patient 1 to be imaged. For example, housing 25 may house various components that generate and apply gradient fields and RF radiation bursts at desired frequencies associated with the particular tissue of patient 1 to be imaged.

The strong magnetic field generally orients the protons of patient 1 in particular directions by superimposing position dependent magnetic gradients. However, the RF radiation bursts cause some of the patient's protons to resonate, or spin, at a particular frequency during the application of the RF radiation bursts. The resonance frequency applied by MRI device 20 is referred to as the Larmour frequency which has a linear relationship with the local magnetic field. When an RF radiation burst is terminated, the resonating protons reorient in accordance with the strong magnetic field of MRI device 20, giving off energy in the process. MRI device 20 can detect the energy given off by the reorienting protons to create a high quality image of the tissue or matter of patient 1.

In accordance with the invention, MRI device 20 and pacemaker 10 coordinate operation, in that the pacing or sensing capabilities of pacemaker 10 are used to define timing of the MRI. In particular, the pacing or sensing functions of pacemaker 10 are used to coordinate application of electromagnetic radiation bursts and gradient fields by MRI device 20. For example, one or more wireless signals 28 can be communicated between pacemaker 10 and MRI device 20 to achieve such coordination. In some cases, pacemaker 10 may send signals 28 to MRI device 20 to communicate sensed information, and thereby allow MRI device 20 to make informed decisions about when to apply the electromagnetic radiation bursts and gradient fields. In other cases, MRI device 20 may send signals 28 to pacemaker 10 to cause pacemaker 10 to deliver pulses, i.e., to trigger pacemaker 10 to stimulate heart 5. In still other cases, an external programmer (not shown) may send and receive signals from pacemaker 10, MRI device 20, or both to effectuate coordination of the operation of pacemaker 10 with MRI device 20.

Figure 2:
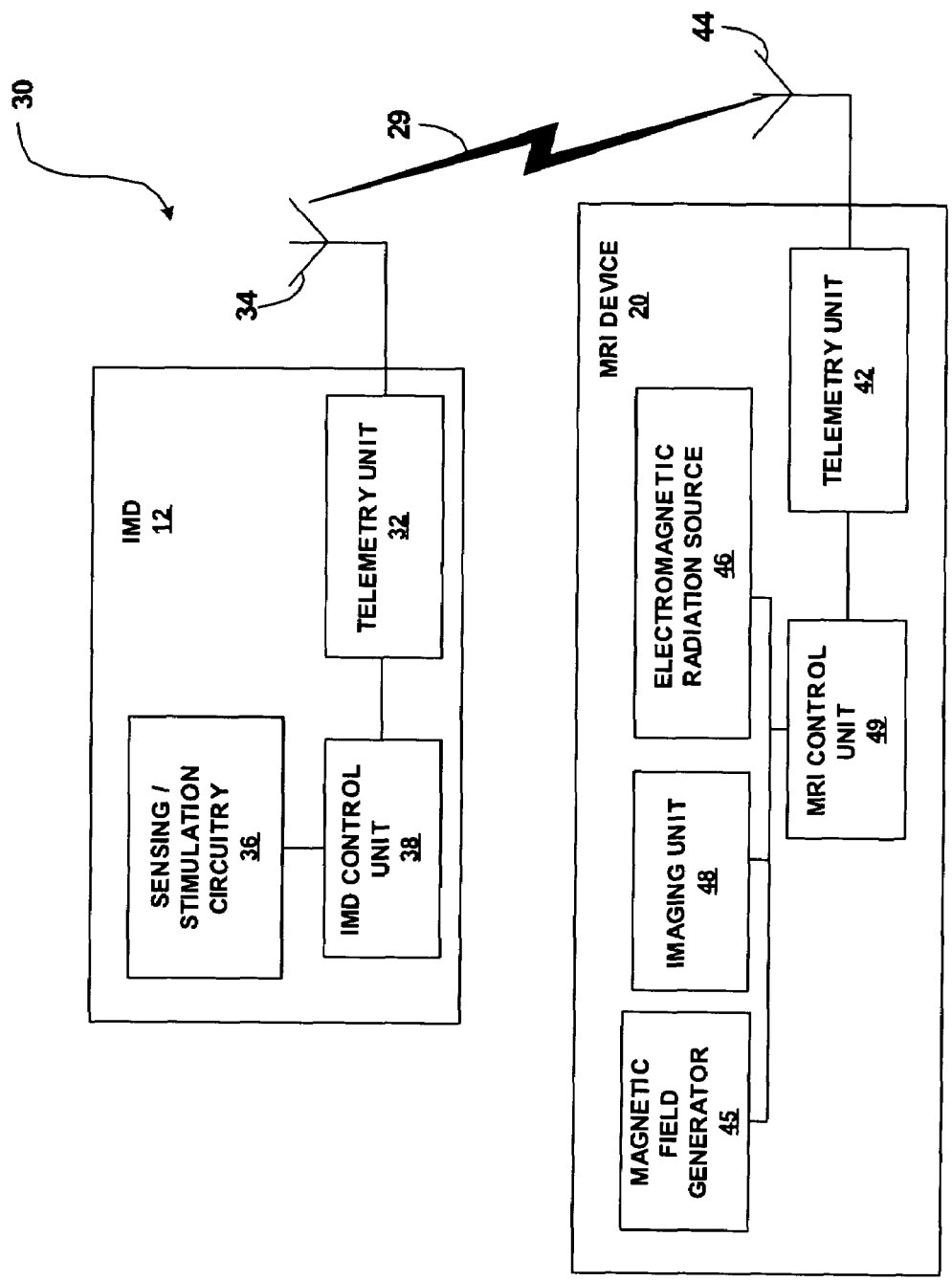
FIG. 2 is a functional block diagram of an MRI device communicating with an IMD.

FIG. 2 is a block diagram illustrating a system 30 that includes an MRI device 20 and an IMD 12 such as pacemaker 10 (FIG. 1). In system 30, MRI device 20 communicates to IMD 12 via wireless signals 29. In particular, any of a wide variety of telemetry techniques may be used to facilitate transfer of information between MRI device 20 to IMD 12. Alternatively an external programmer (not shown) may also be used, e.g., with a wireless connection to IMD 12 and a wired or wireless connection to MRI device 20.

IMD 12 includes a telemetry unit 32 and an antenna 34 to facilitate transmission and reception of wireless signals 29 from MRI device 20. IMD 12 also includes circuitry 36 for sensing and/or stimulating a patient for therapeutic purposes. For example, sensing/stimulation circuitry 36 may include electrodes disposed on medical leads and implanted at locations in a patient where sensing and stimulation occurs. Sensing/stimulation circuitry 36 typically includes one or more amplifiers to enhance the sense signals, and to generate the electrical potentials needed for effective stimulation.

IMD control unit 38 controls circuitry 36 so that sensing and stimulation occurs at proper times. In particular, IMD control unit 38 may define various sensing and stimulation algorithms that control the therapy to be provided. For example, if IMD 12 is a cardiac pacemaker, as in the example of FIG. 1, IMD control unit 38 may execute algorithms that receive sensed information from circuitry 36 and determine whether an arrhythmia has occurred in the heart. If IMD control unit 38 identifies an arrhythmia, it may store this information, and possibly respond by causing circuitry 36 to provide stimulation therapy specifically for the identified arrhythmia. IMD control unit 38 may execute a number of algorithms to identify and respond to a wide variety of potential arrhythmias in the patient's heart.

MRI device 20 includes a telemetry unit 42 and an antenna 44 to facilitate communication of wireless signals 29 with IMD 12. MRI device 20 makes use of electromagnetic fields to create images of a patient. In particular, MRI techniques are particularly useful in creating images of blood flow, images to facilitate identification of cancer, or other images that can not be easily generated via conventional imaging techniques such as X-ray techniques, or the like.

MRI device 20 includes one or more magnetic field generators 45 and one or more electromagnetic radiation sources 46. Magnetic field generator 45 generates a relatively large magnetic field, e.g., in the range of 0.2 to 20 Tesla. Magnetic field generator 45 may include a permanent magnet, an electromagnet, or the like, and may also include gradient field generators to impose gradient fields during the MRI. In addition, MRI device 20 includes one or more electromagnetic radiation sources 46, such as RF radiation sources. As outlined above, MRI device 20 subjects a patient to a very strong magnetic field and gradient magnetic fields via magnetic field generator 45. Electromagnetic radiation source 46 of MRI device 20 then applies pulses or bursts of electromagnetic radiation (typically radio frequency (RF) radiation) to an area of the patient to be imaged. The strong static magnetic field of magnetic field generator 45 generally orients the protons of patient in particular directions, but the RF radiation bursts of electromagnetic radiation source 46 cause some of the patient's protons to resonate with frequency typical for the local magnetic fields. When the RF radiation burst is terminated, the resonating protons reorient in accordance with the strong static magnetic field of the magnetic field generators 45, giving off energy in the process.

Imaging unit 48 of MRI device 20 can receive and detect the energy given off by the reorienting protons. Imaging unit 48 uses the detected energy given off by the reorienting protons to create one or more images of the tissue or matter of the patient. In this manner, MRI device 20 is used to create medical images for display to physicians.

MRI control unit 49 coordinates the application of gradient fields by magnetic field generator 45, RF radiation bursts by electromagnetic radiation source 46, and the imaging by imaging unit 48. In particular, MRI control unit 49 may define the timing of the RF radiation bursts by electromagnetic radiation source 46, including the start time and duration of any given burst. MRI control unit 49 may perform one or more algorithms to coordinate and define the MRI techniques of MRI device 20. In addition, MRI control unit 49 may blank one or more electrical components of MRI device 20 during application of the RF radiation bursts, e.g., to avoid electrical interference or malfunction of the components. Also, IMD 10 may blank one or more of its components during application of the RF radiation bursts. In any event, as outlined in greater detail below, timing of bursts may be defined by information received from IMD 12. Accordingly, MRI control unit 49 may use this information received from IMD 12 in controlling the timing of bursts as described below.

In accordance with the invention, MRI device 20 and IMD 12 communicate with one another to coordinate operation of IMD 12 with application of electromagnetic radiation bursts by MRI device 20. In particular, the stimulating or sensing functions of IMD 12 can be used to coordinate application of electromagnetic radiation bursts by MRI device 20. For example, wireless signals 29 can be communicated between IMD 12 and MRI device 20 to achieve such coordination. In some cases, IMD 12 may send signals 29 to MRI device 20 to communicate sensed information, and thereby allow MRI device 20 to make informed decisions about when to apply the electromagnetic radiation bursts. In other cases, MRI device 20 may send signals 29 to IMD 12 to cause IMD 12 to deliver pulses, i.e., to trigger IMD 12 to stimulate the patient. In still other cases, an external programmer (not shown) may send and receive signals from IMD 12, MRI device 20, or both to effectuate coordination of the operation of IMD 12 with MRI device 20. MRI control unit 49 uses the information received from IMD 12 to control the timing of bursts. Time stamps may be included in the communicated information to compensate for any transmission delays.

Such communication and coordination between IMD 12 and MRI device 20 may improve the MRI process. In particular, IMD 12 may provide more accurate measurements of patient rhythm, and communication of such measurements to MRI device 20 can allow the MRI device to apply electromagnetic radiation bursts at desired times during the patient's rhythm. Alternatively, stimulation may be provided by IMD 12 to trigger patient rhythm in a manner that can improve imaging by MRI device 20.

For example, when using MRI to image a patient's heart, each burst can be timed for application at a common point of the sinus rhythm. In other words, each of a series of MRI electromagnetic radiation bursts can be applied when the heart is in a similar state, i.e., in a common stage of the cardiac cycle. Conventionally, surface electrocardiograms (ECGs) were used to provide measurements of the sinus rhythm and thereby facilitate the coordination of electromagnetic radiation bursts at common times during the cardiac cycle. Surface ECGs, however, can sometimes provide inaccurate cardiac measurements. Moreover, the electromagnetic radiation bursts in MRI may significantly affect ECG readings such that accuracy of the measurements are further undermined. Use of IMD 12 to take measurements of patient rhythm, such as sinus rhythm may therefore improve the MRI process. Moreover, IMD 12 can provide the ability to stimulate the patient and thereby trigger desired rhythm for the MRI.

Figure 3:
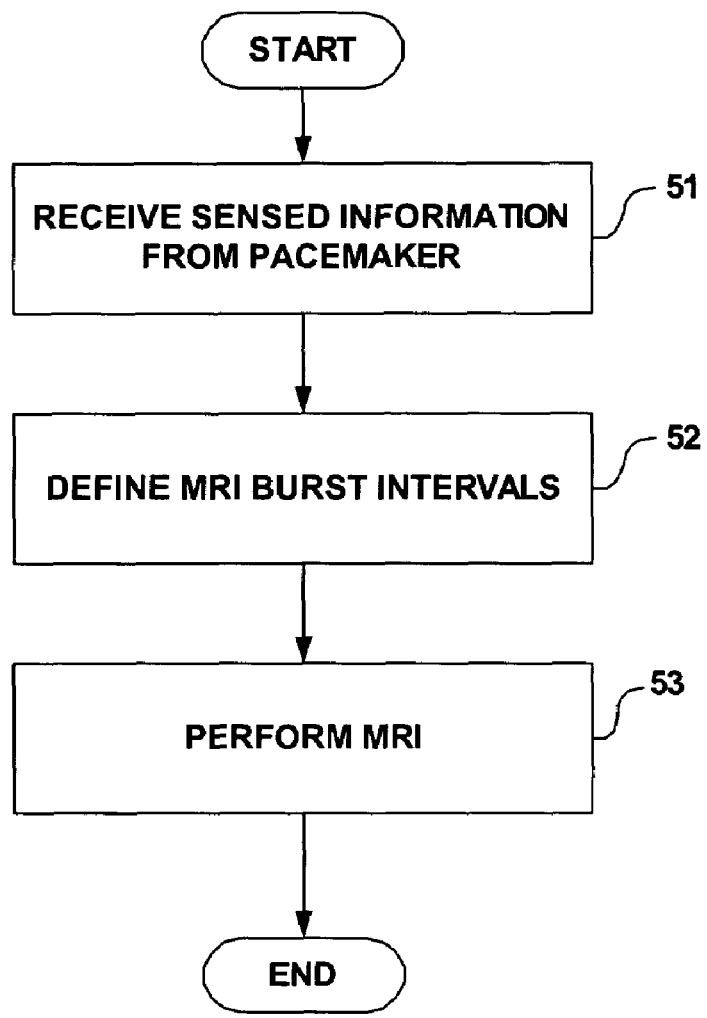
FIGS. 3-5 are flow diagrams illustrating techniques for coordinating MRI techniques with the operation of an IMD according to an embodiment of the invention.

FIG. 3 is a flow diagram illustrating a technique for coordinating MRI techniques with the operation of a pacemaker 10 according to an embodiment of the invention. Similar techniques, however, could also be applied with a wide variety of other IMDs. As shown in FIG. 3, MRI device 20 receives sensed information from pacemaker 10 (51). In particular, electrodes disposed on one or more leads 2 sense electrical events in the heart and this sensed information is sent from pacemaker 10 to MRI device 20. For example, the sensed information may define the occurrence of a P-wave which indicates an atrial depolarization, a QRS complex which indicates a ventricular activation, a T-wave which indicates a ventricular repolarization, or any other signal that can be measured in the heart by pacemaker 10 such as blood pressure, dynamic impedance, blood flow, or the like.

Upon receiving sensed information from pacemaker 10 (51), MRI device 20 controls the timing of MRI electromagnetic burst intervals based on the received information (52). MRI device then performs the MRI (53), by applying electromagnetic radiation bursts and gradient fields at selected times. Because the conditions sensed by pacemaker 10 are used in controlling the timing of application of electromagnetic radiation bursts, the MRI can be improved relative to techniques that measure conditions using surface ECGs. In some cases, both surface ECGs and conditions sensed by pacemaker 10 may be used to define the MRI burst intervals.

In other cases, MRI device 20 may receive one ore more control signals from IMD 10 that cause the bursts to occur. In that case, the IMD 10 would coordinate the MRI to be performed by MRI device 20. The control signals may be sent from IMD 10 with consideration of the latency or time delay associated with the sending, receiving and interpretation of the signal relative to the sensing of patient conditions. The control signal can be viewed as one type of information that can be received from IMD 10 to cause MRI device 20 to apply the electromagnetic radiation bursts at desired times. In some cases, the process of FIG. 3 may continue in a continuous closed loop fashion during the MRI, such that for each image generated, information is received (51), and timing is controlled (52).

Figure 4:
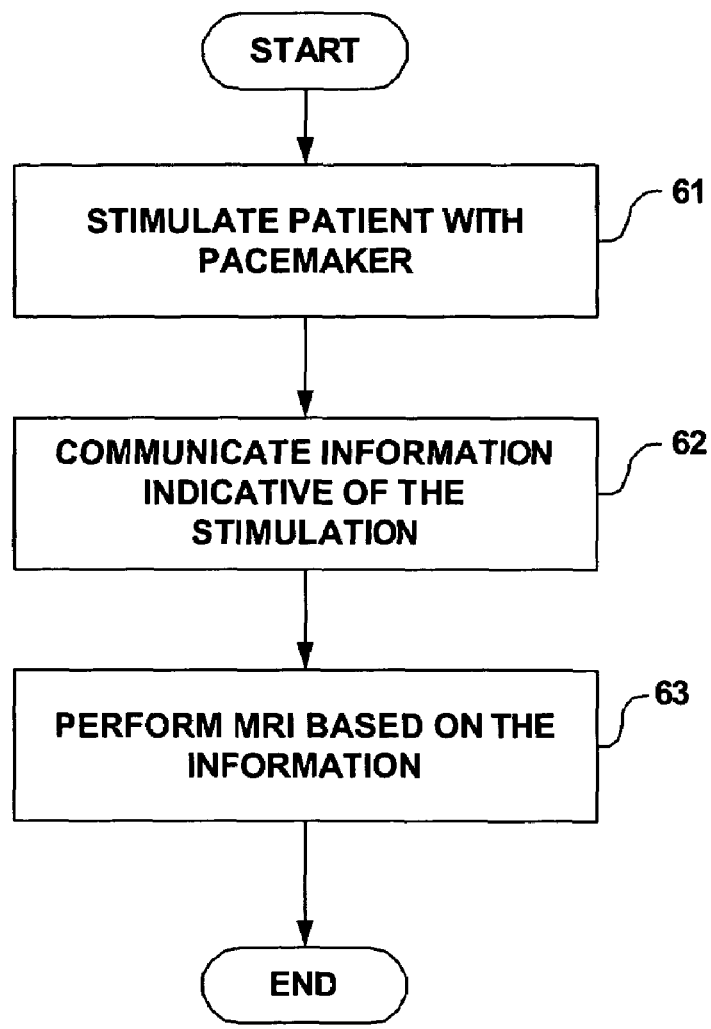

FIG. 4 is another flow diagram illustrating a technique for coordinating MRI techniques with the operation of a pacemaker 10 according to an embodiment of the invention. Again, similar techniques could also be applied with a wide variety of other IMDs. As shown in FIG. 4, pacemaker 10 stimulates a patient (61). In addition, pacemaker 10 communicates information indicative of the stimulation to MRI device 20 (62). For example, pacemaker 10 may communicate timing information indicative of regular pacing stimulus, or may communicate timing information of a particular stimulus, e.g., prior to stimulating the patient (61). In some cases, information may be communicated to achieve clock synchronization between MRI device 20 and pacemaker 10, which could help improve precision of application of the electromagnetic radiation bursts. In any case, MRI device 20 performs the MRI based on the information received from pacemaker 10.

By using pacing stimuli to coordinate the MRI, imaging can be improved. Stimuli may specifically cause the heart to be in the desired interval of the cardiac cycle at a given time. Accordingly, if MRI device 20 is aware of the timing of stimulus to be applied by pacemaker 10, it can apply electromagnetic radiation bursts at specific times that correspond to desired times in the cardiac cycle for a given imaging to occur. In some cases, the particular time or interval of the cardiac cycle during which imaging should occur may depend on the particular MRI being performed and the traits of the heart that a physician wants to examine via the MRI. The process of FIG. 4 may also repeat in a continuous closed loop fashion with the generation of each image of the MRI.

Figure 5:
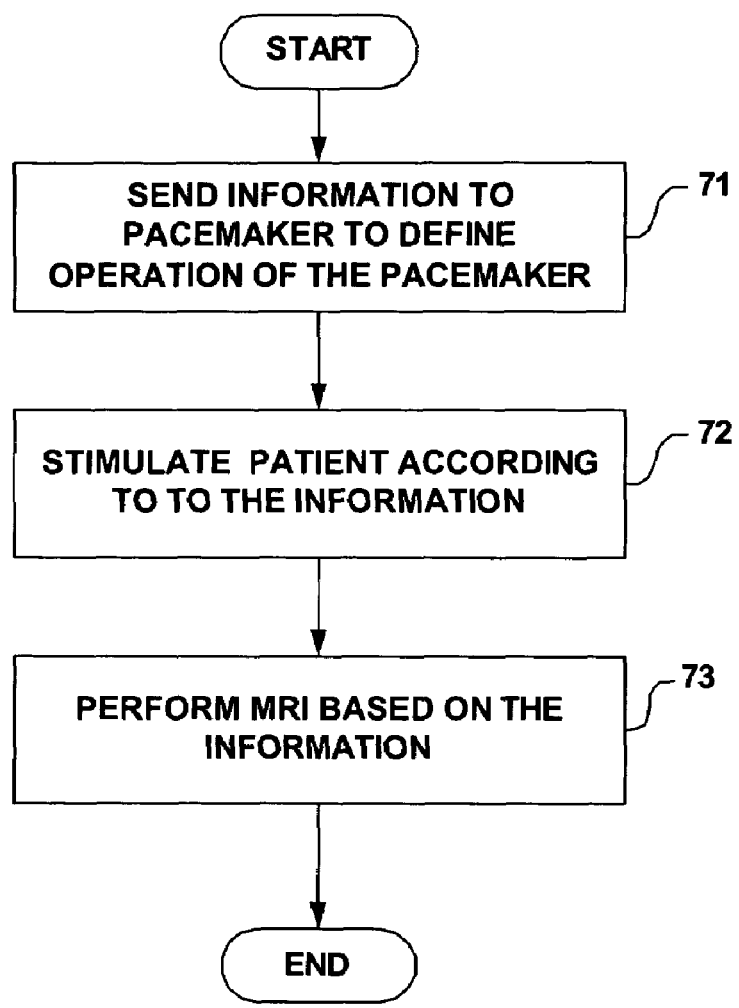

FIG. 5 is another flow diagram illustrating a technique for coordinating MRI techniques with the operation of a pacemaker 10 according to an embodiment of the invention. Again, similar techniques could also be applied with a wide variety of other IMDs. As show in FIG. 5, MRI device 20 (or a programmer) sends information to pacemaker 10 to control operation of pacemaker 10 (71). Pacemaker 10 then stimulates the patient according to the information (72), and MRI device 20 performs the MRI based on the information (73). In other words, stimulation by pacemaker 10 is performed specifically to coordinate application of electromagnetic radiation bursts by MRI device 20. The technique illustrated in FIG. 5 is a triggering technique in that pacemaker 10 is triggered to perform stimulation specifically for MRI. In some cases, the triggered stimulation may be used to invoke a normal sinus rhythm in coordination with application of MRI electromagnetic radiation bursts. In other cases, however, the triggered stimulation may define fast, slow, or even irregular heart activity specifically to enable certain types of MRI imaging. Also, triggered stimulation may purposely invoke an arrhythmia in the patient so that diagnosis of such an arrhythmia can be made. These or other types of triggering could be very useful for certain MRI applications. Like the processes of FIGS. 3 and 4, the process of FIG. 5 may be continuous in that information is sent (71) and stimulation occurs (72) for each image of the MRI.

A number of embodiments of the invention have been described. However, one skilled in the art will appreciate that the invention can be practiced with embodiments other than those disclosed. For example, in addition to sensing or stimulating a patient using an IMD for the purpose of improving MRI, sensed events could also be displayed with an MRI image during the MRI procedure. Display of timing of stimulation near an image during the MRI could also be used as a diagnostic tool. These and other modifications will become apparent to those skilled in the art. The disclosed embodiments are presented for purposes of illustration and not limitation, and the invention is limited only by the claims that follow.

What is claimed is:

1. A method of performing magnetic resonance imaging (MRI) on tissue of a patient having an implantable medical device (IMD) with a telemetry unit communicating timing information as to operational conditions of the IMD, comprising:

receiving the timing information communicated from the (IMD);

applying a plurality of discrete MRI electromagnetic radiation bursts to the tissue of the patient, wherein said applied radiation bursts are synchronized with operational conditions of the IMD based upon the received timing information;

imaging the tissue upon a display, whereby the imaged tissue is displayed in a substantially common state during each of said plurality of radiation bursts, further comprising:

stimulating a patient with the IMD based upon the timing information to produce a specified cardiac rhythm;

imaging the heart tissue based on timing information during application of the stimulation applied to the patient by the IMD; and at least one of storing and displaying at least some of said plurality of images when the heart tissue is at common points during the produced cardiac rhythm.

2. A method according to claim 1, further comprising sensing cardiac activity with the IMD and wherein the timing information includes timing of sensed cardiac activity.

3. A method according to claim 1, further comprising sensing physiologic conditions of the patient with the IMD.

4. A method according to claim 1, further comprising applying cardiac pacing pulses using the IMD and wherein the timing information defines timing of cardiac pacing stimulation pulses applied to the patient by the IMD.

5. The method of claim 1, wherein stimulation based on the timing information is intended to induce an arrhythmia.

6. The method of claim 1, wherein the IMD is a pacemaker and wherein the timing information defines a timing of a cardiac cycle.

7. The method of claim 1, wherein performing the MRI includes applying one or more electromagnetic radiation bursts based on the timing information.

8. The method of claim 1, wherein performing the MRI includes applying one or more gradient magnetic fields based on the timing information.

9. An apparatus comprising:

means for receiving timing information from an cardiac-based implantable medical device (IMD) related to timed operating conditions of the IMD;

means for performing magnetic resonance imaging (MRI) of heart tissue by applying electromagnetic radiation based upon the received timing information; and means for synchronizing application of electromagnetic radiation with the received timing information, whereby the heart tissue being imaged is placed in a substantially common state during each application of radiation, wherein the IMD comprises means for applying cardiac stimulation pulses and wherein the timing information defines timing of cardiac stimulation pulses applied to the patient by the IMD to produce a specified cardiac rhythm and wherein the MRI comprises:

means for imaging the cardiac tissue during application of the cardiac stimulation by the IMD based upon the timing information; and means for storing and displaying a plurality of images taken during common points during the produced cardiac rhythm.

10. An apparatus according to claim 9, wherein the IMD comprises means for sensing cardiac activity wherein the timing information includes timing of sensed cardiac activity.

11. The apparatus of claim 9, wherein cardiac stimulation based on the timing information is adapted to induce an arrhythmia.

12. The apparatus of claim 9, wherein the IMD comprises a pacemaker and wherein the timing information defines a timing of a cardiac cycle.

13. The apparatus of claim 9, wherein the MRI comprises means for applying one or more electromagnetic radiation bursts based on the timing information.

14. The apparatus of claim 9, wherein the MRI comprises means for applying one or more gradient magnetic fields based on the timing information.

* * * * *